United States Patent [19]

Twist et al.

[11] Patent Number: 5,831,001
[45] Date of Patent: Nov. 3, 1998

[54] TREATMENT OF HERPESVIRUS INFECTION

[75] Inventors: Michael Twist, Toronto; Richard W. Barnett, Mississauga; Lorne S. Reid, Toronto; Martin Sumner-Smith, Bolton, all of Canada

[73] Assignee: Allelix Biopharmaceuticals Inc., Mississauga, Canada

[21] Appl. No.: 378,709

[22] Filed: Jan. 26, 1995

Related U.S. Application Data

[63] Continuation of Ser. No. 872,398, Apr. 23, 1992, abandoned, which is a continuation-in-part of Ser. No. 779,735, Oct. 23, 1991, abandoned, which is a continuation-in-part of Ser. No. 602,953, Oct. 24, 1990, abandoned.

[51] Int. Cl.$^6$ .................................................. A61K 38/08
[52] U.S. Cl. ....................... 530/328; 530/329; 530/327; 514/14; 514/15; 514/16
[58] Field of Search ................. 514/12–16; 530/324–329

[56] References Cited

U.S. PATENT DOCUMENTS

| | | | |
|---|---|---|---|
| 4,042,330 | 8/1977 | Deshmukh | 23/230 |
| 4,252,784 | 2/1981 | Levine | 424/9 |
| 4,447,356 | 5/1984 | Olivera | 260/112.5 |
| 4,713,366 | 12/1987 | Stevens | 514/13 |
| 5,093,317 | 3/1992 | Lewis | 514/12 |
| 5,110,802 | 5/1992 | Cantin et al. | 514/44 |
| 5,166,320 | 11/1992 | Wu et al. | 530/395 |
| 5,171,838 | 12/1992 | Chiba | 530/326 |

FOREIGN PATENT DOCUMENTS

| | | |
|---|---|---|
| 8912461 | 12/1989 | WIPO . |
| WO 94/07480 | 4/1994 | WIPO . |

OTHER PUBLICATIONS

Docherty Autimicrob Agents Chemother 31 1562, 1987.
Nahata, "Antiviral Drugs: Pharmachokinetics, Adverse Effects, and Therapeutic Use", Journal of Pharmacy Technology, May/Jun. 1987, pp. 100–108.
Arnold, Jr., "Polylysin–Drug Conjugates," Methods in Enzymology, vol. 112, pp. 270–285 (1985).
Spatola, "Peptide Bond Modifications . . . " Chemistry and Biochemistry of Amino Acids, Peptides & Proteins (Weinstean 1983) 267–357 Ruben et al. (1989) J. Vir. 63(1): 1–8.
Green et al. Cell (Jul. 1989) vol. 58 at 215–223.
Weeks et al. Science vol. 249 1281–1285 (Sep. 1990).
Stryer, (1981) Biochemistry 2:123–127.
Burger J Biol Chem 193, 13, 1951.

*Primary Examiner*—David Lukton
*Attorney, Agent, or Firm*—Foley & Lardner

[57] ABSTRACT

Described herein are oligopeptides useful to inhibit replication of herpesviruses, especially herpes simplex viruses. In a preferred embodiment of the invention, the oligopeptide is a D-arginine nonamer having N- and C-terminal protecting groups, which, at a 5 uM concentration, exhibits greater than 95% inhibition of HSV-1 replication, in a standard assay.

25 Claims, No Drawings

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Modified-site
        ( B ) LOCATION: 6
        ( D ) OTHER INFORMATION: /note= "The Xaa at position 6
            represents a basic amino acid"

( x i ) SEQUENCE DESCRIPTION: SEQ ID NO:1:

Arg Lys Lys Arg Arg Xaa Arg Arg Arg
    1                        5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Modified-site
        ( B ) LOCATION: 2..3
        ( D ) OTHER INFORMATION: /note= "The Xaa at positions 2 and
            3 represents a basic amino acid"

( i x ) FEATURE:
        ( A ) NAME/KEY: Modified-site
        ( B ) LOCATION: 6
        ( D ) OTHER INFORMATION: /note= "The Xaa at position 6
            represents a basic amino acid"

( x i ) SEQUENCE DESCRIPTION: SEQ ID NO:2:

Arg Xaa Xaa Arg Arg Xaa Arg Arg Arg
    1                        5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

Arg Lys Lys Arg Arg Lys Arg Arg Arg
    1                        5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:4:

Arg Lys Lys Arg Arg Ser Arg Arg Arg
    1                        5

( 2 ) INFORMATION FOR SEQ ID NO:5:

( i ) SEQUENCE CHARACTERISTICS:
  ( A ) LENGTH: 9 amino acids
  ( B ) TYPE: amino acid
  ( D ) TOPOLOGY: linear ( x i ) SEQUENCE DESCRIPTION: SEQ ID NO:5:

Arg Lys Lys Arg Arg His Arg Arg Arg
1               5

( 2 ) INFORMATION FOR SEQ ID NO:6:

( i ) SEQUENCE CHARACTERISTICS:
  ( A ) LENGTH: 9 amino acids
  ( B ) TYPE: amino acid
  ( D ) TOPOLOGY: linear ( x i ) SEQUENCE DESCRIPTION: SEQ ID NO:6:

Arg Lys Lys Arg Arg Asn Arg Arg Arg
1               5

( 2 ) INFORMATION FOR SEQ ID NO:7:

( i ) SEQUENCE CHARACTERISTICS:
  ( A ) LENGTH: 9 amino acids
  ( B ) TYPE: amino acid
  ( D ) TOPOLOGY: linear ( i x ) FEATURE:
  ( A ) NAME/KEY: Modified-site
  ( B ) LOCATION: 6
  ( D ) OTHER INFORMATION: /note= "The Xaa at position 6
        represents homoGln"

( x i ) SEQUENCE DESCRIPTION: SEQ ID NO:7:

Arg Lys Lys Arg Arg Xaa Arg Arg Arg
1               5

( 2 ) INFORMATION FOR SEQ ID NO:8:

( i ) SEQUENCE CHARACTERISTICS:
  ( A ) LENGTH: 9 amino acids
  ( B ) TYPE: amino acid
  ( D ) TOPOLOGY: linear ( x i ) SEQUENCE DESCRIPTION: SEQ ID NO:8:

Arg Lys Lys Arg Arg Arg Arg Arg Arg
1               5

( 2 ) INFORMATION FOR SEQ ID NO:9:

( i ) SEQUENCE CHARACTERISTICS:
  ( A ) LENGTH: 9 amino acids
  ( B ) TYPE: amino acid
  ( D ) TOPOLOGY: linear ( x i ) SEQUENCE DESCRIPTION: SEQ ID NO:9:

Arg Lys Arg Arg Arg Arg Arg Arg Arg
1               5

( 2 ) INFORMATION FOR SEQ ID NO:10:

( i ) SEQUENCE CHARACTERISTICS:
  ( A ) LENGTH: 9 amino acids
  ( B ) TYPE: amino acid
  ( D ) TOPOLOGY: linear ( x i ) SEQUENCE DESCRIPTION: SEQ ID NO:10:

Arg Arg Lys Arg Arg Arg Arg Arg Arg
1               5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:11:

```
Arg  Arg  Lys  Arg  Arg  Lys  Arg  Arg  Arg
 1                  5
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:12:

```
Arg  Arg  Arg  Arg  Arg  Lys  Arg  Arg  Arg
 1                  5
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:13:

```
Arg  Gln  Arg  Arg  Arg  Arg  Arg  Arg  Arg
 1                  5
```

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:14:

```
Arg  Arg  Gln  Arg  Arg  Arg  Arg  Arg  Arg
 1                  5
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:15:

```
Arg  Arg  Arg  Gln  Arg  Arg  Arg  Arg  Arg
 1                  5
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:16:

```
Arg  Arg  Arg  Arg  Gln  Arg  Arg  Arg  Arg
 1                  5
```

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:17:

```
Arg  Arg  Arg  Arg  Arg  Gln  Arg  Arg  Arg
1                     5
```

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:18:

```
Arg  Arg  Arg  Arg  Arg  Arg  Gln  Arg  Arg
1                     5
```

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:19:

```
Arg  Arg  Arg  Arg  Arg  Arg  Arg  Gln  Arg
1                     5
```

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:20:

```
Arg  Arg  Arg  Gln  Arg  Arg  Arg
1                     5
```

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:21:

```
Arg  Arg  Arg  Arg  Arg  Arg  Arg
1                     5
```

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:22:

```
Arg  Arg  Arg  Arg  Arg  Arg  Arg  Arg
1                     5
```

( 2 ) INFORMATION FOR SEQ ID NO:23:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:23:

Arg Arg Arg Arg Arg Arg Arg Arg Arg
1               5

(2) INFORMATION FOR SEQ ID NO:24:

(i) SEQUENCE CHARACTERISTICS:
    (A) LENGTH: 10 amino acids
    (B) TYPE: amino acid
    (D) TOPOLOGY: linear (xi) SEQUENCE DESCRIPTION: SEQ ID NO:24:

Arg Arg Arg Arg Arg Arg Arg Arg Arg Arg
1               5                   10

(2) INFORMATION FOR SEQ ID NO:25:

(i) SEQUENCE CHARACTERISTICS:
    (A) LENGTH: 11 amino acids
    (B) TYPE: amino acid
    (D) TOPOLOGY: linear (xi) SEQUENCE DESCRIPTION: SEQ ID NO:25:

Arg Arg Arg Arg Arg Arg Arg Arg Arg Arg Arg
1               5                   10

(2) INFORMATION FOR SEQ ID NO:26:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:26:

Arg Arg Arg Arg Arg Arg Arg Arg Arg Arg Arg Arg
1               5                   10

(2) INFORMATION FOR SEQ ID NO:27:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:27:

Tyr Gly Arg Lys Lys Arg Arg Gly Arg Arg Arg Pro
1               5                   10

(2) INFORMATION FOR SEQ ID NO:28:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:28:

Tyr Gly Arg Lys Lys Arg Arg Cys Arg Arg Arg Pro
1               5                   10

(2) INFORMATION FOR SEQ ID NO:29:

(i) SEQUENCE CHARACTERISTICS:
    (A) LENGTH: 12 amino acids

-continued (B) TYPE: amino acid
(D) TOPOLOGY: linear (xi) SEQUENCE DESCRIPTION: SEQ ID NO:29:

Tyr Gly Arg Lys Lys Arg Arg Ser Arg Arg Arg Pro
1               5                       10

(2) INFORMATION FOR SEQ ID NO:30:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:30:

Tyr Gly Arg Lys Lys Arg Arg His Arg Arg Arg Pro
1               5                       10

(2) INFORMATION FOR SEQ ID NO:31:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:31:

Tyr Gly Arg Lys Lys Arg Arg Lys Arg Arg Arg Pro
1               5                       10

(2) INFORMATION FOR SEQ ID NO:32:

(i) SEQUENCE CHARACTERISTICS:
    (A) LENGTH: 12 amino acids
    (B) TYPE: amino acid
    (D) TOPOLOGY: linear (xi) SEQUENCE DESCRIPTION: SEQ ID NO:32:

Tyr Gly Arg Lys Lys Arg Arg Asn Arg Arg Arg Pro
1               5                       10

(2) INFORMATION FOR SEQ ID NO:33:

(i) SEQUENCE CHARACTERISTICS:
    (A) LENGTH: 12 amino acids
    (B) TYPE: amino acid
    (D) TOPOLOGY: linear (ix) FEATURE:
    (A) NAME/KEY: Modified-site
    (B) LOCATION: 8
    (D) OTHER INFORMATION: /note= "The Xaa at position 8
        represents homoGln"

(xi) SEQUENCE DESCRIPTION: SEQ ID NO:33:

Tyr Gly Arg Lys Lys Arg Arg Xaa Arg Arg Arg Pro
1               5                       10

TREATMENT OF HERPESVIRUS INFECTION

CROSS REFERENCE TO THE RELATED APPLICATION

This application is a continuation of application Ser. No. 07/872,398, filed Apr. 23, 1992; which is a continuation-in-part of application Ser. No. 07/779,735, filed Oct. 23, 1991, now abandoned, which in turn is a continuation-in-part of application Ser. No. 07/602,953, filed Oct. 24, 1990 now abandoned.

FIELD OF THE INVENTION

This invention relates to anti-viral compounds. More particularly, the invention relates to the use of peptide-based anti-viral agents for the treatment of herpesvirus infections.

BACKGROUND OF THE INVENTION

The herpesviruses constitute a family of human pathogens related by a number of criteria, including life cycle, host range, polypeptide composition and genome structure. The herpesvirus family includes the herpesviridae that are divided into three sub-families; α-herpesvirinae which includes herpes simplex virus (HSV) type 1, which manifests as cold sores and type 2 which causes genital lesions, pseudorables virus, equine abortion virus, and infectious bovine rhinotracheitis virus; α-herpesvirinae which includes human and murine cytomegalovirus (CMV); and gamma-herpesvirinae which includes the Epstein-Barr virus (EBV) which is responsible for infectious mononuleosis. Also included in the herpesvirus family is the Varicella Zoster virus (VZV) which is the causative agent of chicken pox, and the recently discovered human herpesviruses HHV-6 and HHV-7.

The current types of herpes treatments are reviewed in "Antiviral Drugs; Pharmacokinetics, Adverse Effects and Therapeutic Use", M. C. Nahata, J. Pharm. Technol., 1987, 3:100. Among current anti-herpetic agents are acyclovir, and structurally related nucleoside analogues. The association of anti-herpetic activity with peptides has been noted, but is less common. In U.S. Pat. No. 4,845,195, Colonno et al ascribe anti-herpetic activity to the pentapeptide Val-Val-Asn-Asp-Leu and various analogues (see also U.S. Pat. No. 4,837,304).

Although some significant advances have been made in the treatment of herpesvirus infections, the need for effective, safe therapeutic agents for treating herpesvirus infections continues to exist.

It is a general object of the present invention to provide a method useful to treat herpesvirus infection in a mammal.

It is a more specific object of the present invention to provide a method useful to treat infection by a herpes simplex virus (HSV).

It is another object of the present invention to provide a pharmaceutical composition useful to treat herpesvirus infection.

It is another object of the present invention to provide a compound useful to inhibit herpesvirus replication.

SUMMARY OF THE INVENTION

It has now been found that oligopeptides that are substantially basic in nature i.e. have a substantially positive net charge, are particularly effective as inhibitors of herpesvirus replication, it has further been found that the anti-herpetic activity of such oligopeptides is not significantly reduced when amino acid components of such oligopeptides are in the more serum-stable D-amino acid form.

According to one aspect of the present invention, there is provided a compound capable of inhibiting herpesvirus replication, of the formula:

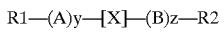

wherein
R1 is H or an N-terminal protecting group;
R2 is OH or a carboxyl terminal protecting group;
X represents an oligopeptide consisting of 'n' amino acids and having a net positive charge selected from N, N–1 and n–2, wherein n is an integer from 6 to 12;
y is 0 or 1;
z is 0 or 1; and
A and B independently represent one or more amino acids residues which collectively are selected to retain the anti-herpetic nature of the compound.

According to one embodiment of the invention, X in the above formula represents an oligopepide comprising at least one D-amino acid, and more desirably consists essentially of D-amino acids. A preferred compound of the present invention consists of nine D-arginine residues having blocking groups at both the N- and C-termini.

According to another aspect of the invention, there is provided a pharmaceutical composition comprising a physiologically acceptable carrier and an effective amount of an anti-herpetic compound of the present invention. In embodiments of the present invention, the pharmaceutical composition is provided in a form suitable for topical or systemic administration.

According to another aspect of the present invention, there is provided a method for treating a patient infected with a herpesvirus, which comprises administering to the patient an effective amount of an anti-herpetic compound of the present invention. In embodiments of the present invention, the anti-herpetic compound is administered to treat herpesvirus infection in humans or for veterinary purposes, particularly for the treatment of livestock.

DETAILED DESCRIPTION OF THE INVENTION AND ITS PREFERRED EMBODIMENTS

The present invention provides oligopeptide-based compounds having anti-herpetic activity, for use in the treatment of herpesvirus infections. The term "oligopeptide" is used interchangably with the term "polypeptide", and refers to a compound having from 6 to about 100 or more amide-linked α-amino acid residues. As slated hereinabove, the term "herpesvirus " is intended to embrace the various members of the herpesvirus family, which unless otherwise indicated herein, refers collectively to species including all types of herpes simplex virus (HSV) such as HSV-1 and HSV-2, the varicella zoster viruses, and the Epstein-Barr viruses. The term "anti-herpetic" refers to the ability of a given compound to inhibit replication of at least one member of the herpesvirus family, as determined by a cell culture assay used conventionally in the art, such as the well established plaque reduction assay. In the context of the plaque reduction assay for example, the anti-herpetic nature of a given compound is indicated by a reduction in plaque count following treatment of virally infected cells with the given compound, relative to a virally infected control.

In one of its aspects, the present invention provides a family of anti-herpetic oligopeptide-based compounds, of the formula:

R1—(A)y—[X]—(B)z—R2     (I)

wherein
R1 is H or an N-terminal protecting group;
R2 is OH or a carboxyl terminal protecting group;
X represents an oligopeptide consisting of 'n' amino acids and having a net positive charge of 'n', 'n–1' or 'n–2', wherein n is an integer from 6 to 12;
y is 0 or 1;
z is 0 or 1; and
A and B each represent from 1 to 30 or more independently selected amino acids which collectively are selected to retain the anti-herpetic nature of the compound.

According to one embodiment, compounds of the invention belong to the family represented by the formula (Ia):

R1—[X]—R2     (Ia)

in which R1, R2 and X are as specified above. Preferred are compounds of formula (Ia) in which one of R1 and R2 is a protecting group.

A particularly preferred family of compounds is represented by the formula (Ib), Np—[X]—Cp     (Ib)

in which X is as specified above, Np represents an N-terminal protecting group, and Cp represents a C-terminal protecting group. The term "N-terminal protecting group" refers to a radical attached to the nitrogen atom which serves to protect the amino terminus of the oligopeptide from undesired biochemical attack. The term "C-terminal protecting group" refers to a radical attached to the C-terminus of the oligopeptide either via an oxygen or via the carbon of the terminal carboxyl group, which senses to protect the carboxyl terminus of the oligopeptide from undesired biochemical attack.

In each of the above formulae I, Ia and Ib, X represents an oligopeptide consisting of 'n' amino acids and having a net positive charge of $\geq$n–2, i,e., a net positive charge of 'n', 'n–1' or 'n–2'. In other words, X is an oligopeptide which consists either entirely of positively charged amino acids (in the case where the net positive charge is 'n') or consists of substantially all positively charged amino acids (in the case where the net positive charge is 'n–1' and 'n–2'). The term "net positive charge" refers to the charge on the oligopeptide X as a whole, and is calculated simply by adding the number of positively charged amino acids resident in oligopeptide X and subtracting from that total the number of non-positively charged amino acids resident in oligopeptide X. For instance, an oligopeptide X in which all but one amino acid is positively charged will have a "net" positive charge of 'n–1' in the case where the one amino acid has a neutral charge. The net charge on oligopeptide X will be 'n–2' in the case where the one amino acid has a negative charge. A charge of 'n–2' is also realized when two amino acids carrying a neutral charge are incorporated among otherwise positively charged amino acids. For the purposes of calculating net positive charge, the term "positively charged" refers to an amino acid having a same chain, possibly a β-carbon side chain but usually an α-carbon side chain, that is cationic in aqueous solution and at neutral pH. The term "negatively charged" refers to an amino acid having a side chain that is anionic in aqueous solution and at neutral pH. Amino acids having a neutral charge carry a side chain that exhibits either no charge (e.g. Alanine) or both ± charge (e.g. Glutamine) in aqueous solution and at neutral pH.

Generally, the terms "amino acid" and "α-amino acid residue" are used interchangably herein with reference to naturally occurring and synthetic amino acids in either D- or L- form. Unless otherwise stated, the amino acid is the naturally occurring L-amino acid. Included, unless otherwise stated, are; (1) the amino acids having a neutral charge such as glycine; those amino acids having an aliphatic α-carbon side chain, such as alanine, valine, norvaline, leucine, norleucine, isoleucine and proline; those having aromatic α-carbon side-chains such as phenylalanine, tyrosine and tryptophan; (2) the negatively charged amino acids, including those having acidic α-carbon side chains such as aspartic acid and glutamic acid; those having side chains which incorporate a hydroxyl group such as serine, homoserine, hydroxynorvaline, hydroxyproline and threonine; those having sulfur-containing α-carbon side chains such as cysteine and methionine; and those having side chains incorporating an amide group such as glutamine and asparagine; and (3) the positively charged amino acids, including those having basic α-carbon side chains such as lysine, arginine, histidine, and ornithine (also herein referred to as "basic amino acids").

According to a preferred aspect of the present invention, X comprises at least one amino acid in the D-isomer form. The oligopeptide X may, for example, comprise alternating L- and D-amino acids. Most preferably the oligopeptide consists essentially of D-amino acids.

In specific embodiments of the present invention, oligopeptide X in the above formulae I, Ia and Ib has a sequence selected from among the group consisting of, i) an oligopeptide consisting of from 6 to 11 basic amino acids and one amino acid other than a basic amino acid, wherein each basic amino acid is independently selected from among the group consisting of arginine, lysine, histidine and ornithine, and said one amino acid is selected from among the group consisting of glutamine, serine, histidine, asparagine and homoglutamine. Especially suitable oligopeptides are those in which each basic amino acid is independently selected from arginine and lysine, and the non-basic amino acid is glutamine; and ii) an oligopeptide consisting essentially of from 7 to 12 basic amino acids, wherein each basic amino acid residue is independently selected from among the group consisting of lysine and arginine.

According to specific embodiments of the present invention, X represents an oligopeptide selected from among the group consisting of:

i) an oligopeptide comprising amino acids arranged in the sequence (SEQ ID NO:1) Arg-Lys-Lys-Arg-Arg-Y1-Arg-Arg-Arg, wherein Y1 is a basic amino acid;

ii) an oligopeptide comprising amino acids arranged in the sequence (SEQ ID NO:2) Arg-Y2-Y3-Arg-Arg-Y4-Arg-Arg-Arg wherein each of Y2, Y3 and Y4 is a basic amino acid, and at least one of Y2, Y3 and Y4 is arginine:

iii) an oligopeptide comprising from 6 to 11 arginines and one glutamine; and iv) an oligopeptide homopolymer consisting of from 7 to 12 arginines (SEQ ID NOs. 21–26, respectively).

According to preferred embodiments of the present, invention, X in the above formula I, Ia and Ib represents an oligopeptide, preferably consisting essentially of D-amino acids, having an amino acid sequence selected from: SEQ ID NOs. 3–26, also shown below.

Arg-Lys-Lys-Arg-Arg-Lys-Arg-Arg-Arg;
Arg-Lys-Lys-Arg-Arg-Ser-Arg Arg-Arg;
Arg-Lys-Lys-Arg-Arg-His-Arg-Arg-Arg;
Arg-Lys-Lys-Arg-Arg-Asn-Arg-Arg-Arg;
Arg-Lys-Lys-Arg-Arg-homoGln-Arg-Arg-Arg;
Arg-Lys-Lys-Arg-Arg-Arg-Arg-Arg-Arg;
Arg-Lys-Arg-Arg-Arg-Arg-Arg-Arg-Arg;
Arg-Arg Lys-Arg-Arg-Arg-Arg-Arg-Arg;
Arg-Arg-Lys-Arg-Arg-Lys-Arg-Arg-Arg;
Arg-Arg-Arg-Arg-Arg-Lys-Arg-Arg-Arg;
Arg-Gln-Arg-Arg-Arg-Arg-Arg-Arg-Arg;
Arg-Arg-Gln-Arg-Arg-Arg-Arg-Arg-Arg;
Arg-Arg-Arg-Gln-Arg-Arg-Arg-Arg-Arg;
Arg-Arg-Arg-Arg-Gln-Arg-Arg-Arg-Arg:
Arg-Arg-Arg-Arg-Arg-Gln-Arg-Arg-Arg;
Arg-Arg-Arg-Arg-Arg-Arg-Gln-Arg-Arg;
Arg-Arg-Arg-Arg-Arg-Arg-Arg-Gln-Arg;
Arg-Arg-Arg-Gln-Arg-Arg-Arg-Arg;
Arg-Arg-Arg-Arg-Arg-Arg-Arg-Arg;
Arg-Arg-Arg-Arg-Arg-Arg-Arg-Arg;
Arg-Arg-Arg-Arg-Arg-Arg-Arg-Arg-Arg;
Arg-Arg-Arg-Arg-Arg-Arg-Arg-Arg-Arg-Arg; and
Arg-Arg-Arg-Arg-Arg-Arg-Arg-Arg-Arg-Arg-Arg.

Particularly preferred compounds of the present invention are those of formula I, Ia and Ib in which X represents either homopolymeric D-arginine, having 8, 9 or 10 amide-linked D-arginine residues, or an oligopeptide comprising one at least one D-Gln residue and 7, 8 or 9 D-Arg residues. The presently most preferred compounds are those wherein X in the above formulae I, Ia and Ib represents an oligopeptide consisting essentially of D-amino acids and having an amino acid sequence selected from:

D-[Arg-Lys-Lys-Arg-Arg-Gln-Arg-Arg-Arg];
D-[Arg-Arg-Arg-Arg-Arg-Arg-Arg-Arg-Arg]; and
D-[Arg-Arg-Arg-Gln-Arg-Arg-Arg-Arg-Arg].

As noted hereinabove, the compounds of the present invention are desirably those of formula (Ib)

$$Np—[X]—Cp \qquad (Ib)$$

wherein X represents an oligopeptide as defined above, Np represents an N-terminal protecting group, and Cp represents a carboxyl terminal protecting group. Any chemical group which serves to protect peptide ends from undesired chemical attack can be used. Carboxyl terminal protecting groups and N-terminal protecting groups employed conventionally in the art of peptide synthesis are most desirably incorporated in the compounds of the present invention. Useful N-terminal protecting groups include, for example, lower alkanoyl groups of the formula R—C(O)—wherein R is a linear or branched lower alkyl chain comprising from 1–5 carbon atoms. A preferred N-terminal protecting group is acetyl, CH₃C(O)—. Also useful as N-terminal protecting groups are amino acid analogues lacking the amino function. Preferred amino acid analogs may be represented by the formula S—CH₂—C=O, wherein "S" is a side chain of a naturally occurring amino acid.

Preferred C-terminal protecting groups are, similarly, those used conventionally in the art of peptide synthesis. Such C-terminal protection may be achieved by incorporating the blocking group via the carbon atom of the carboxylic function, for example to form a ketone or an amide, or via the oxygen atom thereof to form an ester. Thus, useful carboxyl terminal protecting groups include, for example, ester-forming alkyl groups, particularly lower alkyl groups such as e.g., methyl, ethyl and propyl, as well as amide-forming amino functions such as primary amine (—NH2), as well as monoalkylamino and dialkylamino groups such as methylamino, ethylamino, dimethylamino, diethylamino, methylethylamino and the like. C-terminal protection can also be achieved by incorporating as the C-terminal amino acid a decarboxylated amino acid analogue, such as agmatine. Of course, N- and C-protecting groups of even greater structural complexity may alternatively be incorporated, if desired.

Especially preferred compounds of the invention, which conform to formula (Ib), are acetyl-[(D-Arg)₉]-NH₂; acetyl-(D-Arg)₃-(D-Gln)-(D-Arg)₅-NH₂; and acetyl-[D-(Arg-Lys-Lys-Arg-Arg-Gln-Arg-Arg-]-NH₂.

It will be appreciated that the oligopeptide may be conjugated, either through its C-terminus or its N-terminus to other amino acids without necessarily sacrificing the anti-herpetic activity exhibited by the oligopeptide, as determined by the assays herein described. The present invention thus further embraces anti-herpetic polypeptide compounds which incorporate the oligopeptides described herein and conform to the general formula (I), i.e.

$$R1—(A)y—[X]—(B)z—R2 \qquad (I)$$

wherein at least one of y and z is 1, A and B independently represent one or more amide-linked, amino acids, and R1, R2 and X are as specified above. Desirably, R1 represents an N-terminal protecting group, Np, and R2 represents a carboxyl terminal protecting group, Cp, wherein Np and Cp are as defined above.

Specifically contemplated compounds of formula I are anti-herpetic compounds in which the oligopeptide X is flanked at the C-terminus and/or at the N-terminus by another unit of oligopeptide X. The repeating units of oligopeptide X may be linked directly by amide bond, or through a peptide linker of from 1 to about 10 amino acids in length.

The compounds of the present invention can be readily prepared by standard, well-established solid-phase peptide synthesis methods (SPPS), general descriptions of which appear, for example, in J. M. Stewart and J. D. Young, *Solid Phase Peptide Synthesis,* 2nd Edition, 1984, Pierce Chemical Company, Rockford, Ill., and in M. Bodanszky and A. Bodanszky, *The Practice of Peptide Synthesis,* 1984, Springer-Verlag, New York; Applied Biosystems 430A Users Manual, 1987, ABI Inc., Foster City, Calif.

In general, a suitably protected amino acid is attached through its carboxyl group (—COOH) to a derivatized, insoluble polymeric support, e.g. cross-linked polystyrene or polyamide resin. "Suitably protected" refers to the presence of protecting groups on the alpha-amino group (α-NH₂) and side-chain functional group (if present) of the amino acid. Synthesis proceeds in a stepwise, cyclical fashion by successively removing the α—NH₂ protecting group, then coupling an activated amino acid to the newly freed α-NH₂. Activation of the —COOH group of the incoming amino acid can be effected directly via a carbodiimide, e.g. dicyclohexylcarbodiimide (DCC) or diisopropylcarbodiimide (DIC), via formation of the symmetric acid anhydride, or preferably by formation of an "active ester", e.g. hydroxybenzotriazole (HOBt), pentafluorophenyl, para-nitrophenyl or N-hydroxysuccinimide esters. Suitable side-chain protecting groups generally are stable to all of the reagents, solvents and reaction conditions used during synthesis, yet removable under conditions which will not affect the integrity of the final peptide product.

The two preferred methods of solid phase peptide synthesis are the BOC and FMOC methods, so called for their use of the tert-butyloxycarbonyl and 9-fluorenylmethyloxycarbonyl groups, respectively, to protect the α-$NH_2$ of the amino acid residues.

In the more established BOC method, the acid-lability of the BOC group is exploited and trifluoroacetic acid (TFA) treatment is used to effect its removal. The preferred amino acid side-chain protecting groups (for examples see Table 1 below) are relatively stable in weak acid e.g. TFA. Most can be cleaved by very strong acids such as hydrofluoric (HF) or trifluoromethanesulfonic acid (TFMSA ), A few side-chain protecting groups, e.g. His(Dnp) & Met(O), may require a separate deprotection step, e.g. thiophenol or ammonolysis, mercaptopyridine or mercaptoethanol treatment, respectively. After synthesis, the peptide is typically cleaved from the resin and simultaneously deprotected by HF treatment at low temperature, e.g. 0° C.

TABLE 1

Examples of Side-Chain Protecting Groups Used in SPPS by the BOC Method

| Residue | Side-Chain Moiety | Protecting Group |
| --- | --- | --- |
| Arginine | guanidino | p-toluenesulfonyl (Tos); methoxybenzenesulfonyl (Mts); nitro. |
| Aspartic Acid, Glutamic Acid | carboxyl | ortho-benzyl (OBzl) |
| Cysteine | sulfhydryl/thiol | p-methylbenzyl ($CH_3Bzl$) |
| Histidine | Imidazole N—H | 2,4-dinitrophenyl (Dnp); (Tos) |
| Lysine | amino | 2-chlorobenzyloxycarbonyl (Cl-Z) |
| Methionine | sulfide/thioether | sulfoxide (O); none |
| Serine, Threonine | hydroxy | benzyl (Bzl) |
| Tryptophan | Indole N—H | formyl (CHO) |
| Tyrosine | hydroxy | 2-bromobenzyloxycarbonyl (Br-Z) |

In the more recently developed FMOC method the base labile FMOC group is removed using a mild organic base, e.g. piperidine, thereby allowing the use of side-chain protecting groups which are labile to milder acid treatment, e.g. TFA (for examples see Table 2). An acid labile ether resin such as HMP-resin (para-hydroxymethylphenoxymethyl polystyrene) is used as the solid support, permitting simultaneous cleavage/deprotection in TFA.

TABLE 2

Examples of Side-Chain Protecting Groups Used in SPPS by the FMOC Method

| Residue | Side-Chain Moiety | Protecting Group |
| --- | --- | --- |
| Arginine | guanidino | 4-methoxy-2,3,6-trimethyl-benzenesulfonyl (Mtr); pentamethylchroman-6-sulfonyl |
| Aspartic Acid, Glutamic Acid | carboxyl | t-butyl ester (OtBu) |
| Cysteine | sulfhydryl/thiol | trityl (Trt); acetamidomethyl (Acm) |
| Histidine | Imidazole N—H | Trt |
| Lysine | amino | t-butyloxycarbonyl (BOC) |
| Serine, Threonine, Tyrosine | hydroxyl | t-butyl (t-Bu) |

Suitably protected and/or preactivated D- and/or L-amino acids, derivatized and/or preloaded resins, and all ancillary reagents and solvents required for either BOC or FMOC peptide synthesis are commercially available from several suppliers. In addition, automated peptide synthesizers with optimized, pre-programmed BOC and/or FMOC synthesis cycles are available from numerous commercial sources.

Incorporation of N- and/or C- protecting groups can also be achieved using protocols conventional to solid phase peptide synthesis methods. For incorporation of C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydryamine (MBHA) resin so that, when peptide synthesis is completed, treatment with hydrofluoric acid releases the desired C-terminally amidated peptide. Similarly, incorporation of an N-methylamine protecting group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxy-benzyl alcohol or equivalent linker, can be used for this purpose, with cleavage from the support being effected by TFA in dichloromethane. Esterification of the suitably activated carboxyl function, e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g. $C_4$-, $C_8$-, or $C_{18}$- silica. Such column fractionation is generally accomplished by running linear gradients, e.g. 0–50%, of increasing % organic solvent, e.g. acetonitrile, in aqueous buffer, usually containing a small amount of TFA, e.g. 0.1%. Alternatively, ion-exchange HPLC can be employed to separate peptide species on the basis of their charge characteristics. Column fractions are collected, and those containing peptide of the desired/required purity are pooled together. The peptide is typically then treated to exchange the cleavage acid (e.g. TFA) with a pharmaceutically acceptable acid, such as acetic acid, to provide a water soluble salt of the peptide.

Following purification, it is desirable to analyze the oligopeptide further to ensure its chemical authenticity. This is most conveniently achieved through amino acid composition analysis. To analyze amino acid composition, a sample of purified oligopeptide is completely hydrolysed in aqueous acid, e.g. HCl, and the resulting mixture of amino acids separated, identified and quantitated via HPLC, e.g. Waters Pico-Tag system or automated analyzer, e.g. Beckman 6300 Amino Acid Analyzer. A more definitive measure of authenticity is full sequence analysis of the peptide. Several protein sequenators which sequentially degrade the peptide and identify the linear order of its amino acids are used for this purpose, and are available from several commercial sources. High-resolution mass spectrometry methods can also be applied, to generate exact molecular weight information.

For use in treating humans, the oligopeptide compounds of the invention are desirably of "pharmaceutical grade" purity, a term used herein with reference to an oligopeptide preparation which has been shown to migrate as a single peak on HPLC, to exhibit uniform and authentic amino acid composition and sequence upon analysis thereof, and which otherwise meets standards set by the various national bodies which regulate quality of pharmaceutical products. It will be appreciated that strict standards of purity may not be required for use of the compounds in the veterinary field.

The present invention provides, in another of its aspects, anti-herpetic compositions that comprise a physiologically tolerable carrier and an effective amount of an anti-herpetic compound of the invention. In this context, the term "effective amount" means an amount of the compound sufficient to cause a reduction in replication of the viral target. Such reduction is most properly revealed by assaying virus titer in serum samples derived from the patient, before and after treatment.

For the treatment of humans infected with herpesvirus, compounds exhibiting pharmaceutical grade purity are combined with pharmaceutically acceptable carriers to generate compositions suitable for administration. Any of the carriers conventionally used in the pharmaceutical industry particularly for peptide-based drugs may be employed, such as diluents, excipients and the like. Reference may be made to "Remington's Pharmaceutical Sciences", 17th Ed., Mack Publishing Company, Easton, Pa., 1985 for guidance on drug formulations generally. According to one embodiment of the invention, the compounds are formulated for administration by injection, either sub-cutaneously or intravenously, and are accordingly provided as aqueous solutions in sterile and pyrogen-free form and optionally buffered or made isotonic. Thus, the compounds may be administered in distilled water or, more desirably, in saline or 5% dextrose solution. The compounds herein designated as preferred compounds are substantially water-soluble. Water solubility of these and other compounds of the invention may be enhanced, if desired, by incorporating a solubility enhancer, such as cetyltrimethylammonium bromide or chloride. Lyoprotectants, such as mannitol, sucrose or lactose and buffer systems, such as acetate, citrate and phosphate may also be included in the formulation, as may bulking agents such as serum albumin.

Alternatively, the compounds of the present invention may be formulated for administration by routes other than injection, of course. Compositions for topical application, such as creams, lotions or ointments can be used, as may aerosol inhalable formulations. Oral dosage forms, such as tablets, capsules and the like, formulated in accordance with standard pharmaceutical practise, may also be employed. Cream, lotion and ointment formulations will be useful particularly for application to virally-induced skin lesions. Appropriate triglyceride bases and gels can be used to prepare creams and ointments, and surfactants and antimicrobial agents may be incorporated, as is conventional.

The present invention provides, in another of its aspects, a method for treating a a mammal, including a human, infected with a herpesvirus, which comprises the step of administering to the mammal a pharmaceutical composition comprising an effective amount of an anti-herpetic compound of the present invention. According to one embodiment of the invention, the method is applied for the purpose of treating a human patient, in a specific embodiment of the invention, the patient is one diagnosed as having a herpes simplex virus infection, especially an HSV-1 infection. In accordance with another embodiment of the present invention, the mammal is a cow, pig, sheep or other livestock infected with a herpesvirus infection. Suitable treatment regimens are those which maintain at the desired site e.g. in the infected tissue or at a localized skin surface, an amount of the compound sufficient to control herpesvirus replication. The precise dosage sizes appropriate for treatment can readily be established in appropriately controlled trials. It is anticipate that an effective treatment regimen for patients infected with herpesvirus will involve the systemic administration of dosage sizes in the range from 0.01 mg to about 10 mg per kg, e.g., between about 0.1 mg/kg to about 5 mg/kg. It will be appreciated however, that effective dosage sizes will vary according to the route of administration, and the frequency of administration. For example, topical formulations, which remain localized at the infected site, may be administered less frequently. Suitable topical formulations are expected to contain the anti-herpetic compound at a concentration of from about 0.1 to 50 mg/ml, e.g. about 1–10 mg/ml.

EXAMPLE 1

Oligopeptides of series 1 noted below were synthesized by, and purchased from, the American Peptide Company, using the solid phase peptide synthesis approach, and in accordance with protocols conventional thereto. More particularly, synthesis was performed on a Beckman 990 synthesizer, using chloromethyl-polystyrene as solid support, and Boc-base protocols and protecting groups to generate the following compounds;

1A) (SEQ ID NO:27) Tyr-Gly-Arg-Lys-Lys-Arg-Arg-Gly-Arg-Arg-Arg-Pro
1B) (SEQ ID NO:28) Tyr-Gly-Arg-Lys-Lys-Cys-Arg-Arg-Arg-Pro
1C) (SEQ ID NO:29) Tyr-Gly-Arg-Lys-Lys-Arg-Arg-Ser-Arg-Arg-Arg-Pro
1D) (SEQ ID NO:30) Tyr-Gly-Arg-Lys-Lys-Arg-Arg-His-Arg-Arg-Arg-Pro
1E) (SEQ ID NO:31) Tyr-Gly-Arg-Lys-Lys-Arg-Arg-Lys-Arg-Arg-Arg-Pro
1F) (SEQ ID NO:32) Tyr-Gly-Arg-Lys-Lys-Arg-Arg-Asn-Arg-Arg-Arg-Pro
1G) (SEQ ID NO:33) Tyr-Gly-Arg-Lys-Lys-Arg-Arg-homoGln-Arg-Arg-Arg-Pro Oligopeptides in series 2 as noted below were also purchased from American Peptide Company, and were synthesized by BOC chemistry and purified using conventional procedures, to yield the acetate salt of the following compounds:

2A) Arg-Gln-Arg-Arg-Arg-Arg-Arg-Arg-Arg
2A.5) (SEQ ID NO:14) Arg-Arg-Gln-Arg-Arg-Arg-Arg-Arg-Arg
2B) (SEQ ID NO:15) Arg-Arg-Arg-Gln-Arg-Arg-Arg-Arg-Arg
2B.5) (SEQ ID NO:16) Arg-Arg-Arg-Arg-Gln-Arg-Arg-Arg-Arg
2C) (SEQ ID NO:17) Arg-Arg-Arg-Arg-Arg-Gln-Arg-Arg-Arg
2D) (SEQ ID NO:19) Arg-Arg-Arg-Arg-Arg-Arg-Arg-Gln-Arg

Synthesis and evaluation of an L-Arg nonamer was also undertaken. Nona-L-arginine, (L-Arg)$_9$ (SEQ ID NO:23) was prepared by the BOC solid-phase synthesis method.

Synthesis was performed by The American Peptide Company using a Beckman 990 synthesizer and chloromethylpolystyrene resin as solid support.

The tert-butyloxycarbonyl group (BOC) was used to protect the α-NH$_2$ function of L-arginine during the synthesis. The guanidino function was protected with the para-toluenesulfonyl group (Tos). Couplings were carried out using excess hydroxybenzotriazole (HOBt)-activated ester of BOC-L-Arg(Tos), Removal of the BOC protecting group after each cycle was effected with TFA. The final peptide, (L-Arg)$_9$ (SEQ ID NO:23) was cleaved from the polymer resin and the Tos protecting groups removed via standard HF treatment. After removal of HF, the peptide+resin mixture was washed with diethyl ether and extracted with aqueous acetic acid.

The crude peptide was lyophilized, then fractionated by RP-HPLC on a C$_{18}$ silica column using a gradient of 2–40% acetonitrile in 0.1% TFA. Fractions were collected and checked by analytical RP-HPLC. Those containing ≧95% of the major product were combined. High resolution mass spectrometry showed the product to be the expected L-(Arg)$_9$(SEQ ID NO:23).

EXAMPLE 2

A number of compounds containing D-amino acids were also synthesized for analysis, as outlined below:

4A) D-(Arg-Lys-Lys-Arg-Arg-Gln-Arg-Arg-Arg)

The named D-peptide, designated 4A, is readily prepared by the FMOC solid-phase synthesis method and an automated synthesizer, e.g. Applied Biosystems 430A. α-Amino groups of the D-amino acids are protected with the base-labile fluorenylmethyloxycarbonyl group (FMOC). The lysine and arginine side-chains are protected via acid-labile protecting, e.g. BOC an methoxytrimethylbenzenesulfonyl (MtR), respectively. The C-terminal FMOC-D-Arg(Mtr) residue is double-coupled to a suitably derivatized polystyrene resin, e.g. HMP-polystyrene, via the symmetric anhydride. Removal of the FMOC group is carried out in 20% piperidine. Addition of amino acid residues to the peptide-resin is effected via their activated HOBt esters. Cleavage and deprotection of the final peptide is carried out by treatment with TFA. The crude peptide is purified by RP-or ion exchange HPLC. The purified product is characterized by standard amino acid analysis and/or mass spectrometry and/or sequence analysis.

4C) acetyl-[D-Arg]$_9$-NH$_2$

The title compound, designated compound 4C, was synthesized using p-methylbenzhydrylamine (MBHA) resin as solid support, to provide the C-terminal blocking amine on the resultant peptide. Synthesis proceeded using D-arginine residues in which the amino function was blocked with the t-BOC group, and the guanidino function was blocked with the Tos group. Coupling cycles and deprotection were performed as described for the L-Arg nonamer. When coupling cycles were completed, the resin-bound peptide was treated with 20% acetic anhydride in acetonitrile, to incorporate an acetyl protecting group at the N-terminus thereof. Liberation of peptide from the resin, and removal of Tos groups, were achieved by treatment with hydrofluoric acid, yielding the c-terminally amidated, title compound. After removal of hydrofluoric acid, the resin/peptide mixture was washed with diethyl ether and extracted with aqueous acetic acid. The crude peptide was lyophilized, and then purified by RP-HPLC fractionation as described for the L-Arg nonamer. High resolution mass spectrometry showed the product to the desired compound.

Using synthesis protocols just described for synthesis of compound 4C, to incorporate an amidated C-terminus and an acetylated N-terminus, the following additional oligopeptides consisting essentially of D-amino acids were synthesized and purified for testing in the HSV inhibition assay:

4G) acetyl-[D-(Arg-Lys-Lys-Arg-Arg-Gln-Arg-Arg-Arg)]-NH$_2$
4H) acetyl(D-Arg)$_3$-(D-Gln)-(D-Arg)$_5$-NH$_2$
4J) acetyl-[D-(Arg)$_8$]-NH$_2$
4K) acetyl-[D-(Arg)$_7$]-NH$_2$

EXAMPLE 3
Inhibition of HSV replication

Selected compounds were first formulated as 10 mM stocks in water for in vitro and call culture procedures. Then stocks are then diluted into buffers used for specific assays, or into cell culture media. For animal studies peptides are diluted into phosphate buffer saline, The following procedures were then used to determine inhibitory effects of compounds on the replication of HSV. First, confluent monolayers of Veto cells (continuous passage cell line derived from African Green Monkeys) in 24 well cell culture plates were treated with specified concentrations of peptide for 25 hours. This was accomplished by diluting the stock peptide solution in growth medium used to overlay the monolayers, i.e. growth medium containing 10% fetal bovine serum and 10 ug/ml gentamicin in Dulbecco's MEM (DMEM).

After pretreatment with peptide 4C, monolayers were overlaid with 0.1 ml log$_{10}$ dilutions of virus ranging from $10^{-1}$ to $10^{-6}$. Virus was then allowed to adsorb for 1 hour at 37° C. The virus inoculum was removed and the monolayers are overlayed with DMEM containing 2% FBS, 10 ug/ml gentamicin and specified concentration of peptide. Virus was next allowed to replicate for 2 to 3 days until the plaques were judged to be well developed, and then the monolayers were fixed and stained with a solution of 1% crystal violet in 1% formaldehyde, 70% ethanol. Finally, plaques (each representing a single viable virion) were counted and checked microscopically.

Results of the plaque reduction assay performed with compound 4C (acetyl-[D-Arg]$_9$-NH$_2$) are tabulated below:

| Peptide Concentration | Virus titer |
| --- | --- |
| 0.0 | 530.000 pfu/ml |
| 0.5 uM | 30,000 pfu/ml |
| 5.0 uM | 11,000 pfu/ml |

The results show that incubation of the cells with a 5uM concentration of selected oligopeptide induces significant reduction in the herpesvirus replication. At the concentration tested, peptide 4C achieves a 95% or better inhibition of viral replication. There was no apparent inhibition of host cell replication at the concentration when peptide 4C was tested. In separate experiments, a 100 uM concentration of peptide 4C was found to have no significant detrimental effect on cell replication, although some reduction was noted at 500 uM. This indicates that 4C can be formulated and used at therapeutic, non-toxic doses.

We claim:

1. A method for treating a mammal having a herpesvirus infection, which comprises the step of administering to a mammal that is infected with herpesvirus a pharmaceutical composition comprising a carrier and an anti-herpetic amount of a compound sufficient to cause a reduction in herpesvirus replication, of the formula:

R1—(X)—R2 wherein
R1 is selected from the group consisting of H and an N-terminal group selected from a lower alkanoyl and S—CH$_2$—C=O—, where S is a side-chain of a naturally-occurring amino acid;

R2 is selected from the group consisting of OH and a C-terminal group selected from an ester-forming alkyl group and an amide-forming amino group selected from —NH$_2$, monoalkylamino, dialkylamino and an amino acid analogue lacking the carboxyl functionality; and X represents an oligopeptide consisting of 'n' amino acids wherein said oligopeptide has a net positive charge selected from n, n−1 and n−2, and wherein n is an integer from 6 to 12, with the provisos that (a) each amino acid in said oligopeptide is naturally-occurring, or a D-isomer thereof, (b) at least one of said amino acids is an arginine residue, and (c) at least one of said amino acids is a D-isomer,
wherein said composition is in a form suitable to treat said infection and causes a reduction in herpesvirus replication.

2. A method as claimed in claim 1, wherein said composition is administered topically to a herpesvirus-induced skin lesion.

3. A method as claimed in claim 1, wherein said composition comprises the compound acetyl-((D-Arg)$_9$)-NH$_2$.

4. A method as claimed in claim 3, wherein said composition is administered topically to a herpesvirus-induced skin lesion.

5. A method as claimed in claim 3, wherein said mammal is a human and said herpesvirus infection is a herpes simplex virus.

6. A method as claimed in claim 5, wherein said herpes simplex virus infection is a herpes simplex virus type 1 infection.

7. A method as claimed in claim 1, wherein X consists of D-amino acid residues.

8. A method according to claim 7, wherein said compound is selected from acetyl-((D-Arg)$_9$)-NH$_2$, acetyl-(D-Arg)$_3$-(D-Gln)-(D-Arg)$_5$-NH$_2$, and acetyl-(D-(Arg-Lys-Lys-Arg-Arg-Gln-Arg-Arg-Arg))-NH$_2$.

9. A method according to claim 7, wherein X is homo-oligomeric D-arginine.

10. A method according to claim 7, wherein X consists of 7, 8 or 9 D-arginine residues and at least one D-Gln residue.

11. A method as claimed in claim 7, wherein X is an oligopeptide consisting of from 6 to 11 basic amino acids and one amino acid other than a basic amino acid, wherein each basic amino acid is independently selected from the group consisting of arginine, lysine, histidine and ornithine, and said one amino acid other than a basic amino acid is selected from the group consisting of glutamine, serine, asparagine and homoglutamine.

12. A method as claimed in claim 11, wherein each basic amino acid is independently selected from the group consisting of arginine and lysine.

13. A method as claimed in claim 12, wherein the non-basic amino acid is glutamine.

14. A method as claimed in claim 7, wherein X is an oligopeptide consisting of from 7 to 12 basic amino acids, wherein each basic amino acid residue is independently selected from the group consisting of lysine and arginine.

15. A method as claimed in claim 7, wherein X is D-(Arg-Lys-Lys-Arg-Y1-Arg-Arg-Arg), wherein Y1 is a basic amino acid.

16. A method as claimed in claim 7, wherein X is D-(Arg-Y2-Y3-Arg-Arg-Y4-Arg-Arg-Arg), wherein each of Y2, Y3 and Y4 is a basic amino acid.

17. A method as claimed in claim 16, wherein at least one of Y2, Y3 and Y4 is arginine.

18. A method as claimed in claim 7, wherein X is an oligopeptide of from 6 to 11 arginine residues and one glutamine residue.

19. A method as claimed in claim 7, wherein X consists of 7, 8 or 9 D-arginine residues.

20. A method as claimed in claim 7, wherein R1 is selected from the group consisting of H and an N-terminal group selected from a lower alkanoyl group of the formula R—C(O)— wherein R is a linear or branched lower alkyl chain comprising from 1–5 carbon atoms.

21. A method as claimed in claim 20, wherein R2 is selected from the group consisting of OH and a C-terminal group selected from an ester-forming lower alkyl group and an amide-forming amino group selected from —NH$_2$, monoalkylamino and dialkylamino.

22. A method as claimed in claim 7, wherein R1 is acetyl and R2 is NH$_2$.

23. A method as claimed in claim 7, wherein X is an oligopeptide consisting of from 7 to 9 basic amino acids and one amino acid other than a basic amino acid.

24. A method as claimed in claim 7, wherein X is an oligopeptide consisting of from 8 to 10 basic amino acids.

25. A method for treating a mammal having a herpesvirus infection, which comprises the step of administering to a mammal that is infected with herpesvirus a pharmaceutical composition comprising a carrier and an anti-herpetic amount of a compound sufficient to cause a reduction in herpesvirus replication, of the formula:

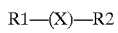

wherein
R1 is selected from the group consisting of H and an N-terminal group selected from a lower alkanoyl and S—CH7—C=O—, where S is a side-chain of a naturally-occurring amino acid;

R2 is selected from the group consisting of OH and a C-terminal group selected from an ester-forming alkyl group and an amide-forming amino group selected from —NH$_2$, monoalkylamino, dialkylamino and an amino acid analogue lacking the carboxyl functionality; and X is Tyr-Gly-Arg-Lys-Lys-Arg-Arg-Z-Arg-Arg-Arg-Pro wherein Z is selected from the group consisting of Gly, Cys, Ser, His, Lys, Asn and homoGln, and wherein at least one of the amino acid residues in X is a D-isomer, and wherein said composition is in a form suitable to treat said infection and causes a reduction in herpesvirus replication.

* * * * *